(12) United States Patent
Beck et al.

(10) Patent No.: US 7,584,001 B2
(45) Date of Patent: Sep. 1, 2009

(54) ELECTRICAL EPIDERMAL STIMULATION DEVICE

(76) Inventors: Kent F. Beck, 1155 E. 1525 N., Layton, UT (US) 84040; James Malmstrom, 130 N. 300 W., Kaysville, UT (US) 84037

( * ) Notice: Subject to any disclaimer, the term of this patent is extended or adjusted under 35 U.S.C. 154(b) by 303 days.

(21) Appl. No.: 10/892,624

(22) Filed: Jul. 16, 2004

(65) Prior Publication Data
US 2005/0015119 A1    Jan. 20, 2005

(51) Int. Cl.
*A61N 1/32* (2006.01)
(52) U.S. Cl. .................... 607/50; 607/145; 607/148
(58) Field of Classification Search .................. 607/2, 607/50, 115, 145, 148; 604/20
See application file for complete search history.

(56) References Cited

U.S. PATENT DOCUMENTS

| | | | | |
|---|---|---|---|---|
| 4,694,840 A | * | 9/1987 | Kairis et al. ................ | 600/548 |
| 5,133,352 A | * | 7/1992 | Lathrop et al. .............. | 607/75 |
| 5,797,969 A | * | 8/1998 | Olson et al. ................. | 607/5 |
| 6,083,250 A | * | 7/2000 | Lathrop ....................... | 607/50 |
| 6,175,763 B1 | * | 1/2001 | Sorenson et al. ............. | 604/20 |
| 6,354,991 B1 | * | 3/2002 | Gross et al. .................. | 600/29 |

* cited by examiner

*Primary Examiner*—Mark W Bockelman
*Assistant Examiner*—Eric D Bertram
(74) *Attorney, Agent, or Firm*—Advantia Law Group; Michael W. Starkweather; Jason P. Webb (57) ABSTRACT

An electrical epidermal stimulation device for treating skin ailments having a power supply configured to provide power to the electrical epidermal stimulator, a first and second electrode configured to provide an electrical stimulus to an area of application, a wake up module configured to wake up a control module when a current flows from the first electrode to the second electrode, a voltage step generator module configured to generate a voltage, and an output drive module configured to control a direction of the voltage step to the first and second electrodes. In one embodiment, the electrical epidermal stimulation device comprises an indicator module for notifying a user that the device is functioning. In another embodiment, the voltage step generator module provides a voltage that increases and decreases in predetermined amounts to create a voltage step. In another embodiment, the direction of voltage application switches between the first and second electrodes. In another embodiment, the voltage is applied to the affected area in phases of varying frequency.

16 Claims, 5 Drawing Sheets

ELECTRICAL EPIDERMAL STIMULATION DEVICE

BACKGROUND OF THE INVENTION

1. Field of the Invention

The present invention relates to medical devices. Specifically, the present invention relates to an electrical epidermal stimulation device and method of using the same.

2. Description of the Related Art

The need for an effective treatment of skin lesions caused, for example, by herpes virus is amply demonstrated by the fact that nearly 100 million American citizens are affected by the virus in at least one of two forms, Herpes Simplex I and Herpes Simplex II. Herpes Simplex I is customarily associated with herpes virus infections above the waist, primarily in and around the mouth, while Herpes Simplex II accounts for a high percentage of the genital infections. In both instances of infection the physical manifestation of the occurrence of a lesion is signaled by a tingling or burning sensation at the lesion site at least 24 to 48 hours prior to an actual outbreak of the lesion in the tissue. This tingling sensation is accompanied by an increased reddening of the tissue followed by the appearance of vesicles which subsequently break and form a crust. Unless the lesion becomes infected with a secondary infection the skin will clear and appear normal again within about eight to fourteen days from the onset of the lesion formation.

Various treatment protocols have been developed for the topical treatment of herpes virus lesions, particularly those lesions associated with Herpes Simplex II. These include the use of drying agents such as alcohol, spirits of camphor, and ether, or ointments, creams, topical anesthetics, and antiseptic solutions. Other topical agents that include Idoxuridine, Trifluorothymidine, or Acyclovir have been found to be somewhat effective. However, at present, all of these treatment modalities have been shown to be only marginally effective against the disease, much to the extreme discomfort of the patient. Further, many of these chemical treatment modalities are accompanied by potentially serious side effects.

It can be seen that there is a need for a device and method for effectively treating herpes and other skin irritations. Specifically, there is a need for an electrical epidermal stimulation device that is compact in size and that provides a stepping electrical stimulus to the affected area, and which turns on and turns off at a termination of a stepping period, or when the device is place on or removed from the affected area.

SUMMARY OF THE INVENTION

The present invention has been developed in response to the present state of the art, and in particular, in response to the problems and needs in the art that have not yet been fully solved by currently available electrical epidermal stimulation devices. Accordingly, the present invention has been developed to provide an electrical epidermal stimulation device that overcomes many or all of the above-discussed shortcomings in the art.

Specifically, the present invention provides an electrical epidermal stimulation device having a power supply configured to provide power to the electrical epidermal stimulator, a first and second electrode configured to direct an electrical stimulus to an area of application, a wake up module configured to wake up a control module when a current flows from the first electrode to the second electrode, a voltage step generator module configured to generate a voltage, and an output drive module configured to control a direction of the voltage step applied to the electrodes.

In one embodiment, the electrical epidermal stimulation device comprises an indicator module for notifying a user that the device is functioning.

In another embodiment, the voltage step generator module provides a voltage that increases and decreases in predetermined amounts to create voltage steps.

In another embodiment, the first and second electrodes alternately apply the voltage to the area of application in a first and second direction.

In another embodiment, the voltage is applied to the area of application in phases of varying frequency.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention, as well as other features and advantages not listed, will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Figure 1:
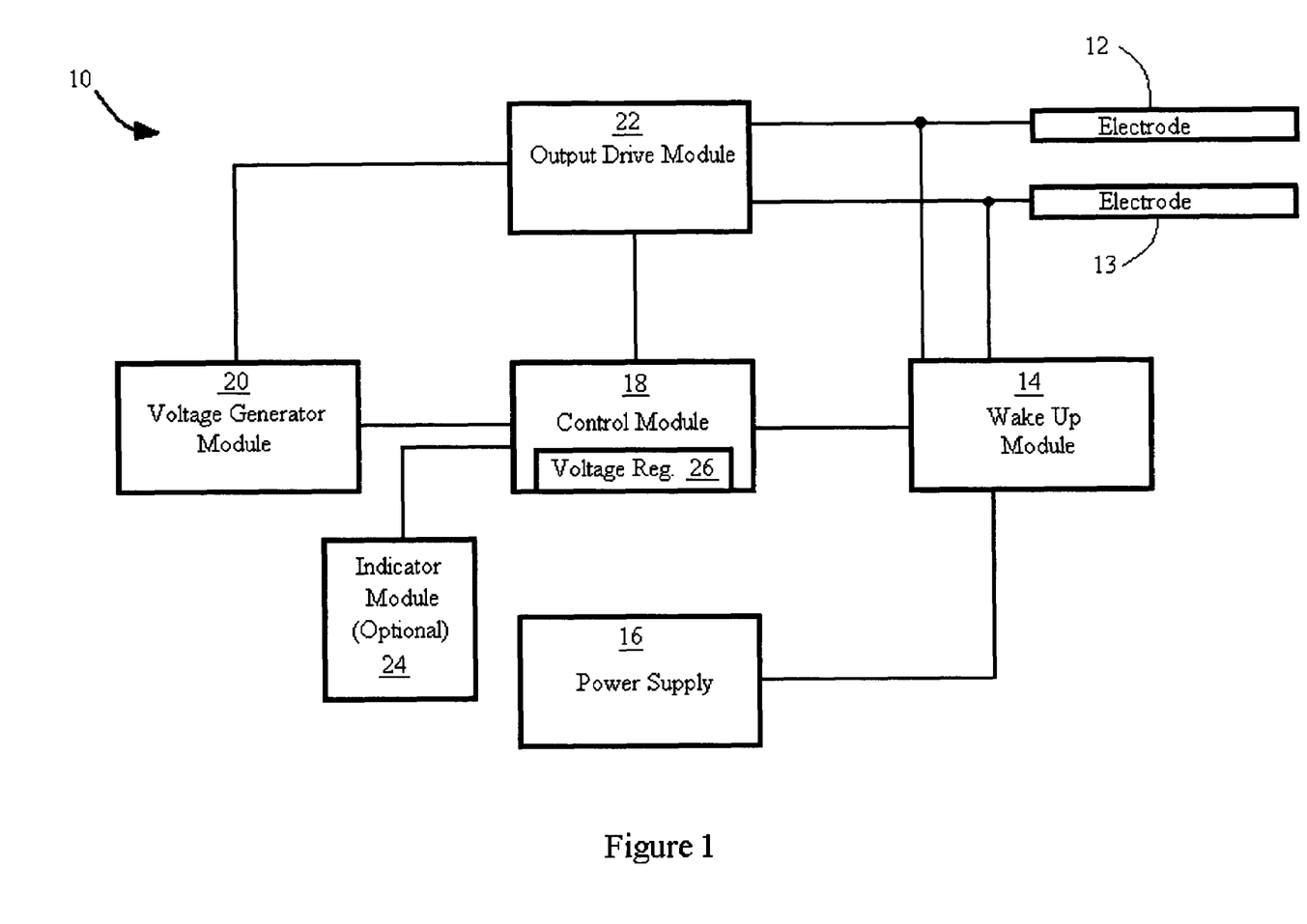
FIG. 1 illustrates a block diagram of an electrical epidermal stimulation device according to one embodiment of the present invention.

FIG. 1 illustrates a block diagram for an electrical epidermal stimulation device 10 ("device") according to one embodiment of the present invention. The device 10 comprises a power supply 16 configured to provide power to the device 10, a first and second electrode 12 and 13 configured to provide an electrical stimulus to an area of application (not shown), a wake up module 14 configured to wake up a control module 18 when a current flows from the first electrode 12 to the second electrode 13, a voltage step generator module 20 configured to generate a voltage, and an output drive module 22 configured to control a direction of the voltage through the first and second electrodes 12 and 13.

While not in use, the device 10 is in a "sleep mode." In "sleep mode," the power source 16 applies power to the wake up module 14 and the first electrode 12 while the second electrode 13, control module 18, voltage step generator module 20, and output drive module 22 remain un-powered. When a user (not shown) places the first and second electrodes 12 and 13 over the area of application, resistance between the first and second electrodes 12 and 13 decreases. The current passes from the first electrode 12 to the second electrode 13 and the voltage is applied to the area of application. When the current passes from the first electrode 12 to the second electrode 13, the wake up circuit 14 awakens the remaining modules, specifically, the control module 18, the voltage step generator module 20, and the output drive module 22.

The control module 18 disables the wake up module 14 so that power is no longer applied from the wake up module 14 to the first electrode 12. The voltage step generator module 20 generates a voltage, which passes to the output drive module 22. The control module 18 signals the output drive module 22 to apply the voltage to the first and second electrodes 12 and 13 in one direction with the voltage from the voltage step generator module 20.

Figure 2:
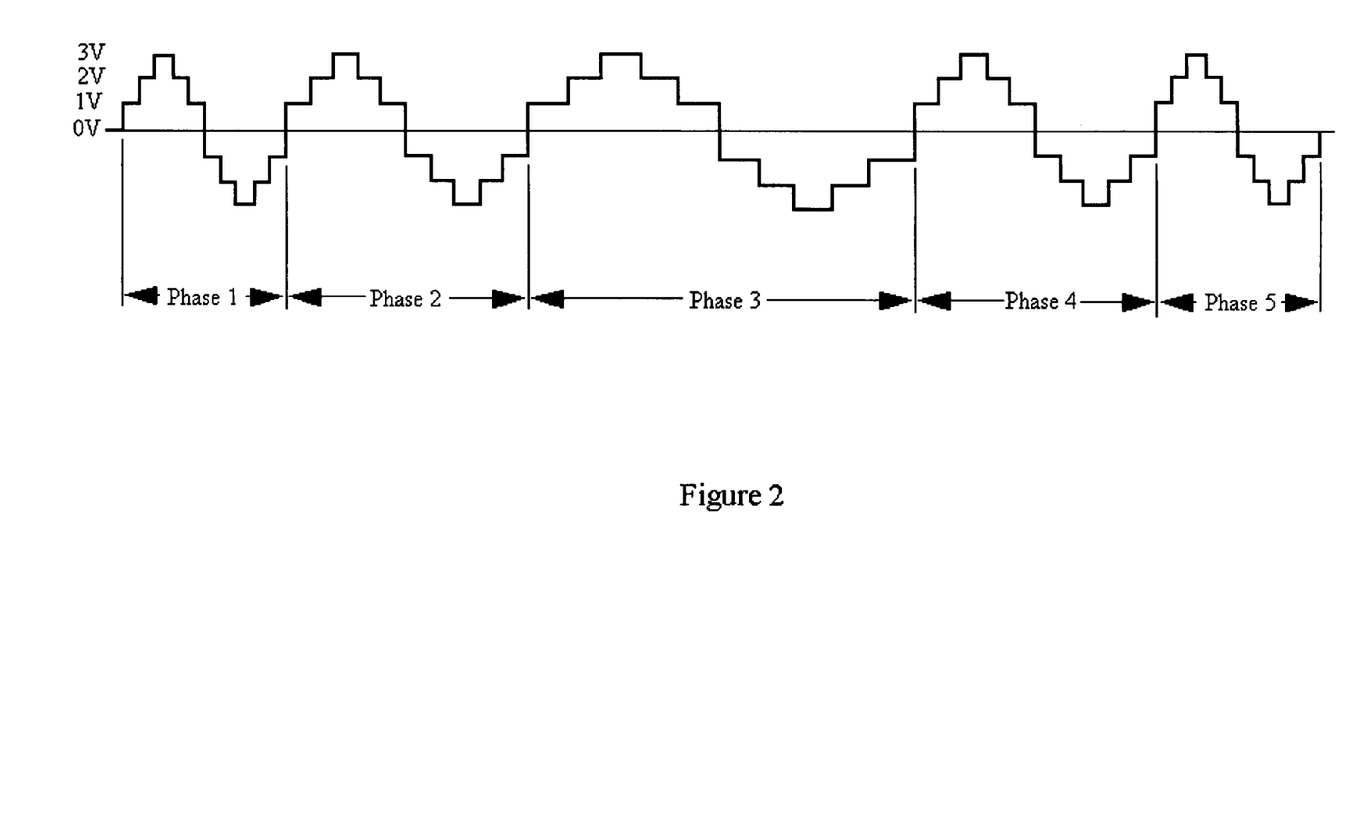
FIG. 2 illustrates an example of a typical application voltage step and phase frequency according to one embodiment of the present invention.

FIG. 2 illustrates an example of a voltage step and phase frequency according to one embodiment of the present invention. In reference to both FIGS. 1 and 2, the voltage step generator module 20 generates the voltage used to stimulate the area of application. The voltage step generator module 20 generates each voltage step up and down, for a predetermined period of time, and increases and decreases the voltage, successively, in stepping motion. The output drive module 22 outputs the voltage to one of the first and second electrodes 12 and 13. The output drive module 22 is configured to switch the direction of the voltage from the voltage step generator module 20. For example, the output drive module 22 applies the voltage to the first electrode 12 with respect to the second electrode 13, for a series of voltage steps, then reverses the direction of the voltage to be applied to the second electrode 13 with respect to the first electrode 12 for another series of voltage steps. Therefore, the user is not required to remove the device 10 from the area of application and reverse the device 10 to apply the voltage in an opposite direction, unlike other types of electrical epidermal devices.

In the illustrated embodiment, and by way of example only, the voltage applied to the first electrode 12 to the second electrode 13 ramps up in three steps. At each step, the voltage is applied to the area of application for a predetermined amount of time. After reaching a maximum voltage of three volts, for example, the voltage applied to the first electrode 12 ramps down in three steps, in decreasing voltage for a predetermined amount of time until the voltage step generator module 20 generates zero volts. Subsequently, the voltage is applied to the second electrode 13 to the first electrode 12 and ramps down in three more steps, in increasing voltage for each step. Again, at each step, the voltage is applied to the area of application for a predetermined amount of time. After reaching a maximum voltage of three volts, the voltage applied to the second electrode 13 ramps up in three steps, in decreasing voltage for each step. Again, at each step, the voltage is applied to the area of application for a predetermined amount of time. The sequence of voltage steps from the first electrode 12 to the second electrode 13, and vice versa, continues for five phases.

Referring still to FIG. 2, the illustrated embodiment shows five phases or stages, labeled as phases 1. 2, 3, 4, and 5. According to the illustrated embodiment, a half phase includes a voltage application, in three successively increasing intensities, followed by three successively decreasing intensities applied through the first electrode 12 to the second electrode 13. In a second half of each phase, a voltage application is applied in three successively increasing intensities, followed by three successively decreasing intensities applied through the second electrode 13 to the first electrode 12. In other words, each phase may comprise three steps up and six steps down, followed by three steps up. One skilled in the art will recognize that any number of steps may be used and that phases can start at any given step and not just as illustrated. As used in herein and as illustrated in FIG. 2, a phase or stage includes a set of voltage steps each having the same period or duration. Accordingly, a change in duration of a voltage step from a previous voltage step indicates the end of one stage and the beginning of another stage.

It is noted that the phases vary with respect to time. For example, phase 1 is illustrated as four seconds, phase two is illustrated as six seconds, phase 3 is illustrated as twenty seconds, and the remaining phases decrease in time where phase 4 is illustrated as six seconds, and phase 5 is illustrated as four seconds. The phases described are for illustration purposes and are not intended to be limiting. Any phase can be applied for any period of time and the phases do not need to be symmetrical.

The control module 18 may be configured to measure the actual voltage between the first and second electrodes 12 and 13 at any time to determine a proper stepping sequence based on a predetermined maximum voltage level. When the measured voltage output through the first and second electrodes 12 and 13 equals the predetermined maximum or minimum intensity, the voltage step generator module 20 stops stepping the voltage up or down.

Figure 3:
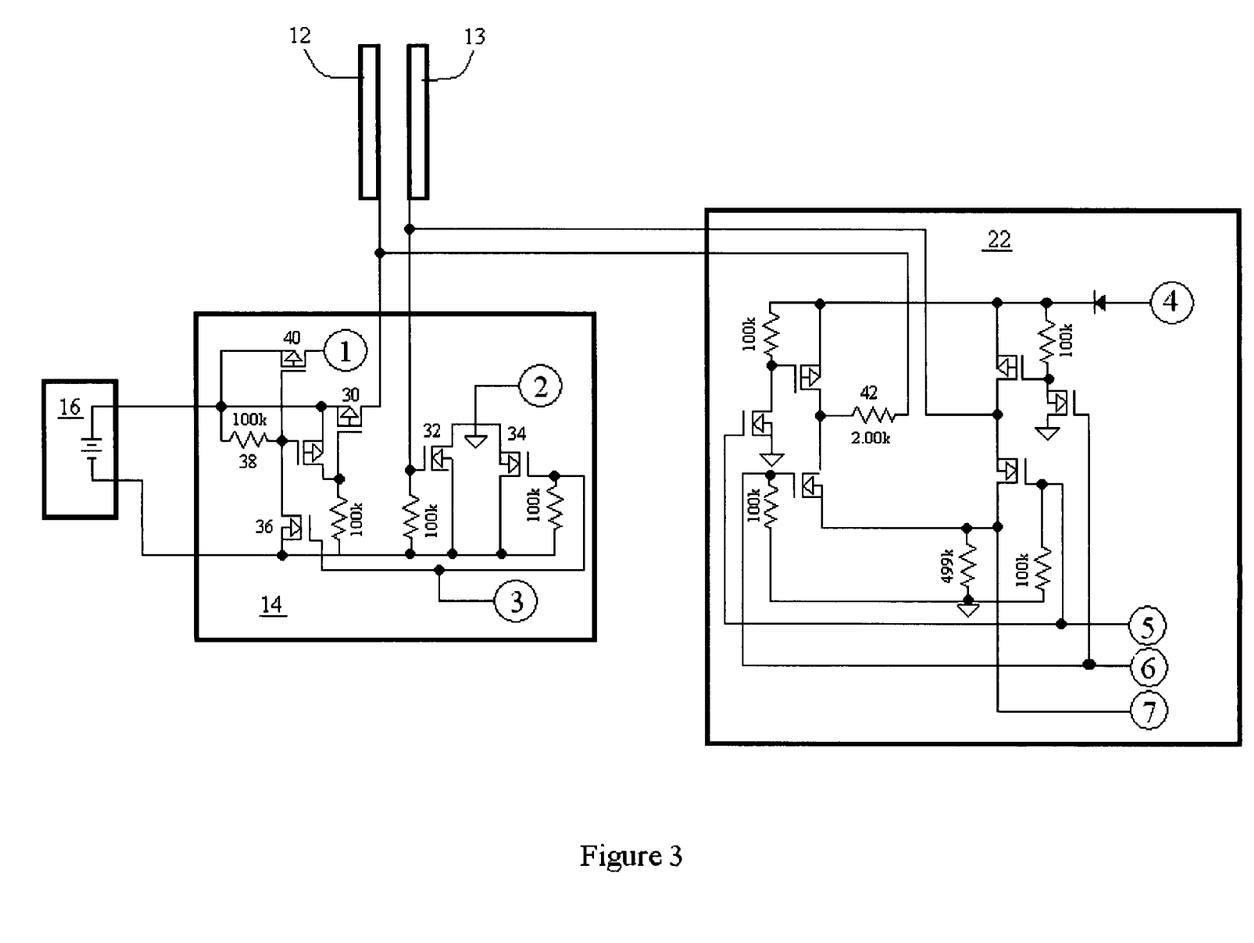
FIG. 3 illustrates a detailed electrical schematic diagram of a wake up module and output drive module of the electrical epidermal stimulation device according to one embodiment of the present invention.

FIG. 3 illustrates a detailed electrical schematic diagram of the wake up module 14 and output drive module 22 of the device 10 according to one embodiment of the present invention. The first and second electrodes 12 and 13 connect to the wake up module 14 and the output drive module 22. Power passes from the power supply 16 through switch 30 of the wake up module 14 to the first electrode 12. As discussed above, in the described state, the device 10 is in sleep mode. When the user (not shown) connects the first and second electrodes 12 and 13, via contact with the skin around the area of application, or some other low impedance connection, the voltage from the power supply 16 transfers from the first electrode 12 to the second electrode 13. Switch 32 turns on after the second electrode 13 receives power, which grounds node 2 (illustrated as a number 2 with a circle placed there around.) Subsequently, nodes 1 and 2 transfer power to the control module 18, voltage step generator module 20, and indicator module 24, thus awakening the device 10 from "sleep mode."

When the device 10 awakens from "sleep mode," the control module 18 directs power to node 3, turns off switch 32, turns on switch 34 to maintain ground, and turns on switch 36, which turns off switch 30. With switch 30 turned off, the first electrode 12 no longer receives power directly from the wake up module 14. Power passes to the control module 18, the voltage step generator module 20, and the indicator module 24 through nodes 1 and 2 (See FIG. 4).

It is noted that the first and second electrodes 12 and 13 may be made of any type of conductive material, including but not limited to, carbon fiber, graphite, metal, etc. Additionally, the first and second electrodes may be configured in any type of orientation.

Figure 4:
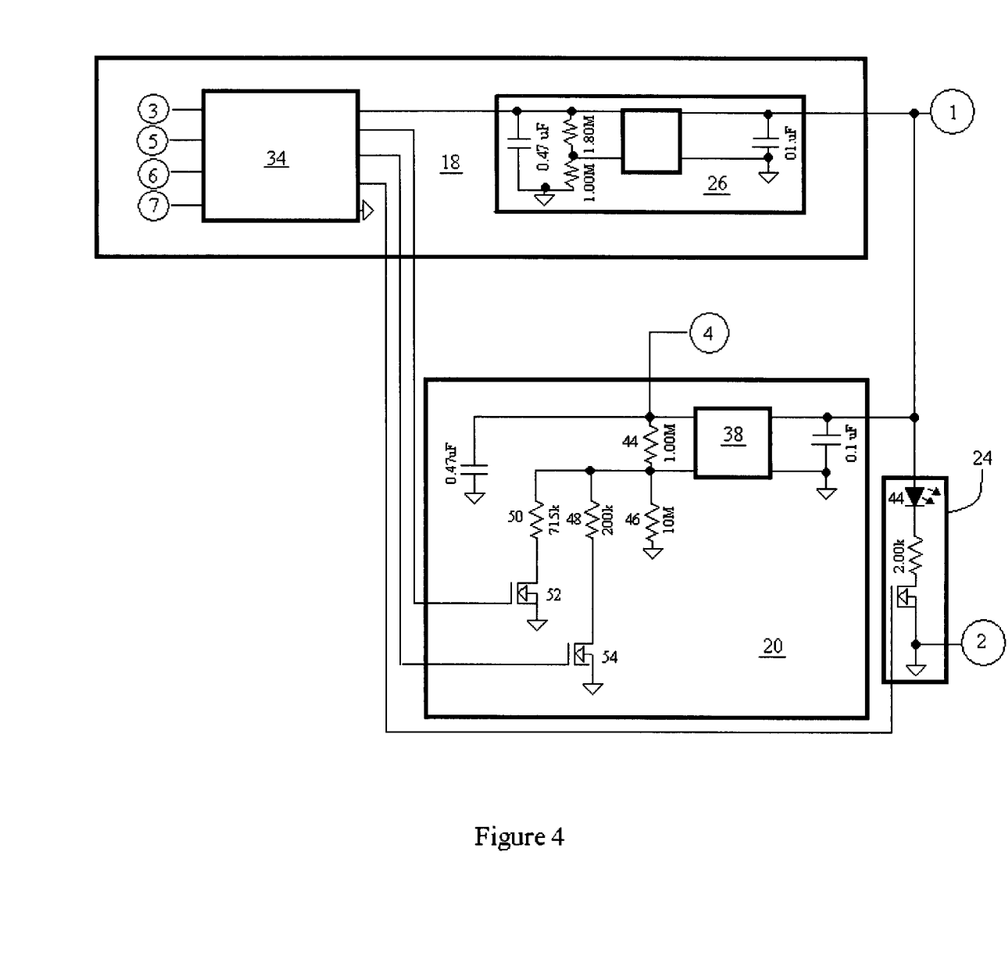
FIG. 4 illustrates a detailed electrical schematic of a control module, voltage step generator module, and indicator module of the electrical epidermal stimulation device according to one embodiment of the present invention.

FIG. 4 illustrates a detailed electrical schematic of the control module 18, the voltage step generator module 20, and the indicator module 24 of the device 10 according to one embodiment of the present invention. Power from the power supply 16 enters through nodes 1 and 2. Node 1 allows power to the control module 18 and the voltage regulator 26 of the control module 18, which supplies power to the processor 34.

Node 1 additionally allows power to the optional indicator module 24 to supply power to a light emitting diode 44 ("LED") or other indicator, such as a speaker. The LED 44 provides notification that the device 10 has been activated. Node 2 allows power to the voltage step generator module 20. The voltage step generator module 20 comprises a voltage regulator 38, which generates the voltages to be applied to the first and second electrodes 12 and 13. As discussed above, the voltage step generator module 20 is configured to provide varying voltage levels, or voltage steps, for predetermined periods of time.

As discussed above, the control module 18 directs power to the wake up module 14 through node 3 and disconnects power to the first electrode 12. The control module 18 directs the voltage step generator module 20 to generate a particular voltage level. The control module 18 also directs the output drive module 22, through nodes 5 and 6, which direction the voltage from node 4 is to be applied across the first and second electrodes 12 and 13. For example, a signal applied to node 5 directs the output drive module 22 to apply the voltage from node 4 to the first electrode 12 with respect to the second electrode 13. A signal applied to node 6 directs the output drive module 22 to apply the voltage from node 4 to the second electrode 13 with respect to the first electrode 12. Therefore, as illustrated in FIG. 3, the output drive module 20 drives the voltage from node 4 to the first and second electrodes 12 and 13, and vice versa, from signals received from the control module 18 through nodes 5 and 6. Accordingly, as discussed above, the user is not required to remove the device 10 and apply the voltage in a reverse direction. Rather, the device 10 accomplishes the task automatically.

Resistor 42 of the output drive circuit is configured to limit the current through the first and second electrodes 12 and 13 so that the full current from the battery is not applied during use.

The processor 34 of the control module 18 monitors the current and voltage through the first and second electrodes 12 and 13 through node 7. If the control module 18 detects no current, the control module 18 puts the device 10 into "sleep mode." Similarly, if the control module 18 measures a voltage at, or above, a predetermined threshold, the voltage step generator module 20 decreases the voltage.

The voltage through node 4, and ultimately through the first and second electrodes 12 and 13, is set by resistors 44, 46, 48, and 50 of the voltage step generator module 20. Accordingly, when the control module 18 requires the lowest voltage, it does not apply a voltage to switches 52 and 54, which leaves resistors 44 and 46 connected. When the control module 18 wants to raise the voltage, the control module 18 turns on switch 52, which places resistor 50 in parallel with resistor 46. The control module 18 can increase the voltage even more by turning off switch 52 and turning on switch 54, which places resistor 50 in parallel with resistor 48 and resistor 46.

When the output drive module 22 finishes applying the voltage through the wave form, as discussed in FIG. 2, the control module 18 removes power on node 3 and the device 10 goes into "sleep mode."

Figure 5:
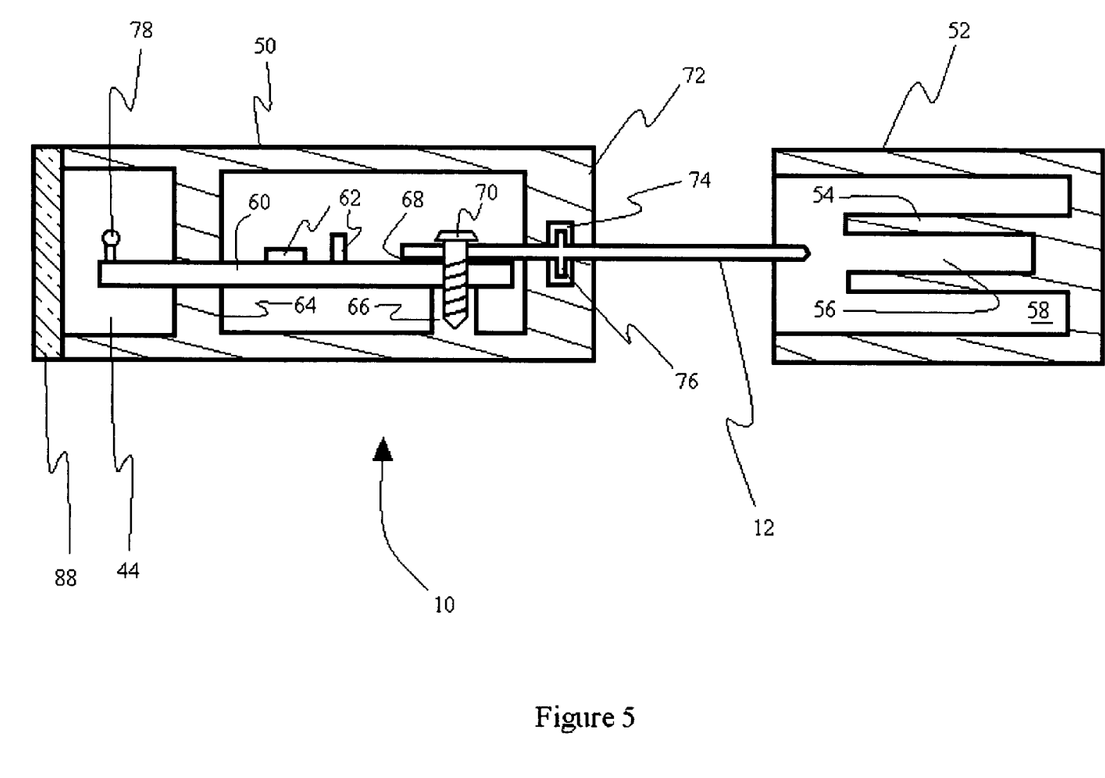
FIG. 5 illustrates a cross sectional side view of the electrical epidermal stimulation device according to one embodiment of the present invention.

FIG. 5 illustrates a cross sectional side view of the device 10 according to another embodiment of the present invention. The device 10 comprises a device housing 50 and a lid 52. The lid 52 is designed to releasably couple to the device housing 50. Optionally, the lid 52 may include an inner wall 54 that forms an electrode cavity 56 to retain the first and second electrodes 12 and 13. In another embodiment, the lid 52 comprises one large cavity 58 rather than an individual electrode cavity 56.

In this embodiment, the device housing 50 is configured to receive a circuit board 60 therein, which contains the wake up module 14, control module 18, voltage step generator module 20, and output drive module 22. The circuit board 60 is mounted on and between holders 64 and 66.

In this embodiment, the first and second electrodes 12 and 13 are mounted to the printed circuit board 60 via electrical pads 68, for example, by solder or pressure fit. A fastener 70, illustrated as a screw, fits through the first electrode 12, through the circuit board 60, and into the holder 66 to tightly retain the first electrode 12 to the pad 68 to ensure electrical contact therebetween.

Additionally, in this embodiment, the first electrode 12 is illustrated to protrude through a front wall 72 of the device housing 50. A cavity 74 in the front wall 72 retains a rib 76 of the first electrode 12 in a substantially fixed position to prevent slippage between the first electrode 12 and the circuit board 60, and to ensure a secure fit to the bond pad 68.

In the illustrated embodiment, the LED 44 is positioned within a cavity 78 of the device housing 10. An end piece 88 may be transparent to allow the user (not shown) to see that the device is functioning. It is envisioned that the LED 44 may be positioned anywhere within the device housing 10. Preferably, the LED 44 is positioned in a location that allows the user to see the LED 44, while the user is using the device 10.

It is understood that the above-described arrangements are only illustrative of the application of the principles of the presently illustrated invention. The present invention may, however, be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

For example, one skilled in the art will understand that any number of phases and/or voltage steps may be incorporated in a treatment, even to the point of eliminating the voltage steps and becoming a wave-like voltage application not having any distinguishable steps.

Although the specification discusses the voltage application being constantly applied to the electrodes, one skilled in the art would easily conceive of many alternatives to having a steady voltage application. For example, a pulsed voltage may be used rather than a constant application.

It is envisioned that any of the modules discussed above could be performed by other modules, such as the wake up function may be performed by the processing module.

Although the illustrated embodiments show first and second electrodes 12 and 13 as protrusions extending from the device 10, it is envisioned that the electrodes may simply be contact points along an edge of the device 10.

Thus, while the present invention has been fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

What is claimed is:

1. An electrical epidermal stimulator, comprising:
a power supply configured to provide power to the electrical epidermal stimulator;
a first and second electrode configured to provide a voltage to an area of application; and
a wake up module electrically coupled to the first and second electrodes and the power supply, and configured to automatically wake up a voltage step generator module of the electrical epidermal stimulator upon detecting a current between the first and second electrodes when the first and second electrodes contact the area of application, to apply the voltage to the area of application, wherein the electrical epidermal stimulator is configured to apply a progressively increasing and decreasing voltage step to the area of application to treat a skin ailment.

2. The electrical epidermal stimulator according to claim 1, wherein the electrical epidermal stimulator is in a sleep mode while the power is applied through the wake up module to the first electrode, and wherein the wake up module automatically wakes up an output drive module.

3. The electrical epidermal stimulator according to claim 1, wherein the electrical epidermal stimulator cuts power to the wake up module after the electrical epidermal stimulator wakes up.

4. The electrical epidermal stimulator according to claim 3, wherein the electrical epidermal stimulator uses a feedback signal from the output drive module to determine the actual voltage being applied to the area of application and either increases or decreases the voltage applied to the area of application in response to the feedback signal received from the output drive module.

5. The electrical epidermal stimulator according to claim 4, wherein the voltage is applied to the area of application in steps until the intensity of electrical stimulation reaches a predetermined maximum level.

6. The electrical epidermal stimulator according to claim 1, wherein each voltage step applies the voltage to the area of application for a predetermined period of time, and wherein the wake up module automatically wakes up an output drive module.

7. The electrical epidermal stimulator according to claim 1, wherein the electrical epidermal stimulator applies the electrical stimulus in at least one stage.

8. The electrical epidermal stimulator according to claim 7, wherein the electrical epidermal stimulator automatically reverses the application of the voltage between the first and second electrodes after each phase.

9. The electrical epidermal stimulator according to claim 8, wherein the electrical epidermal stimulator automatically reverses the direction of the voltage application between the first and second electrodes at least one time per phase.

10. The electrical epidermal stimulator according to claim 1, wherein the electrical epidermal stimulator applies the voltage to the area of application in more than one phase, and the length of time that the voltage is applied to the area of application varies from phase to phase.

11. An electrical epidermal stimulator, comprising:
a power supply configured to provide power to the electrical epidermal stimulator;
a first and second electrode configured to apply a voltage to an area of application;
a wake up module electrically coupled to the first and second electrodes and the power supply, and configured to automatically wake up a voltage step generator module of the electrical epidermal stimulator upon detecting a current between the first and second electrodes when the first and second electrodes contact the area of application, to apply the voltage to the area of application; and
an output drive module electrically coupled to the first and second electrodes, and configured to direct a current flow in a first and second direction through the first and second electrodes, wherein the electrical epidermal stimulator is configured to apply the voltage to the area of application in progressively increasing and decreasing voltage steps to treat a skin ailment, and wherein the wake up module is configured to automatically wake up an output drive module.

12. The electrical epidermal stimulator according to claim 11, wherein the electrical epidermal stimulator uses a feedback signal from the output drive module to determine the actual voltage being applied to the area of application and either increases or decreases the voltage applied to the area of application in response to the feedback signal received from the output drive module, and wherein the wake up module automatically wakes up a control module.

13. The electrical epidermal stimulator according to claim 12, wherein the output drive module automatically reverses the direction of current through the first and second electrodes from the first direction to the second direction when the electrical epidermal stimulator determines that the application of the voltage in the first direction has concluded, and wherein the wake up module automatically wakes up an output drive module.

14. The electrical epidermal stimulator according to claim 11, wherein the electrical epidermal stimulator applies the electrical stimulus in at least one stage.

15. A method of treating a skin ailment using an electrical epidermal stimulator comprising the steps of:
   using a power supply to provide power to the electrical epidermal stimulator;
   using a first and second electrode to provide an electrical stimulus to an area of application;
   using a wake up module to automatically wake up a voltage step generator module of the electrical epidermal stimulator upon detecting a current between the first and second electrodes when the first and second electrodes contact the area of application, to apply the voltage to the area of application; wherein no external manual activation is required to wake up the electrical epidermal stimulator; and
   applying the voltage to the area of application in progressively increasing and decreasing voltage steps to treat a skin ailment.

16. The method according to claim 15, further comprising the step of using an output drive module to control a direction of voltage application between the first and second electrodes, and wherein the wake up module automatically wakes up control module.

* * * * *